United States Patent
Aikens et al.

(10) Patent No.: US 12,364,739 B2
(45) Date of Patent: Jul. 22, 2025

(54) ENZYMES ENTRAPPED IN ORGANOPOLYSILOXANE MATRIX FOR TREATING INTESTINAL DISEASES

(71) Applicant: JL Biosciences, Inc., La Grange, IL (US)

(72) Inventors: John Aikens, La Grange Park, IL (US); LeAnne M. Cabalka Tourtellotte, Valley Village, CA (US)

(73) Assignee: JL Biosciences, Inc., La Grange, IL (US)

( * ) Notice: Subject to any disclaimer, the term of this patent is extended or adjusted under 35 U.S.C. 154(b) by 1074 days.

(21) Appl. No.: 17/253,517

(22) PCT Filed: Jun. 18, 2019

(86) PCT No.: PCT/US2019/037694
§ 371 (c)(1),
(2) Date: Dec. 17, 2020

(87) PCT Pub. No.: WO2019/246070
PCT Pub. Date: Dec. 26, 2019

(65) Prior Publication Data
US 2021/0244801 A1     Aug. 12, 2021

Related U.S. Application Data

(60) Provisional application No. 62/686,734, filed on Jun. 19, 2018.

(51) Int. Cl.
| | | |
|---|---|---|
| *A61K 38/46* | (2006.01) | |
| *A61K 9/16* | (2006.01) | |
| *A61K 9/19* | (2006.01) | |
| *A61K 38/48* | (2006.01) | |

(52) U.S. Cl.
CPC .......... *A61K 38/465* (2013.01); *A61K 9/1641* (2013.01); *A61K 9/19* (2013.01); *A61K 38/4826* (2013.01)

(58) Field of Classification Search
None
See application file for complete search history.

(56) References Cited

PUBLICATIONS

Hartono et al. (J. Phys. Chem. C, 2010, 114, 18, 8353-8362) Functionalized Mesoporous Silica with Very Large Pores for Cellulase Immobilization.*
Chen et al. (Expert Opinion on Therapeutic Patents, 2018, vol. 28, No. 12, 849-865) Quorum sensing inhibitors: a patent review (2014-2018).*

* cited by examiner

*Primary Examiner* — Tigabu Kassa
(74) *Attorney, Agent, or Firm* — Thompson Coburn LLP; Steven M. Ritchey

(57) ABSTRACT

One or more quorum silencing enzymes entrapped in an organopolysiloxane matrix, formulations comprising the enzymes, methods for obtaining the entrapped enzymes by co-gelation and methods of treating intestinal diseases.

5 Claims, No Drawings

ENZYMES ENTRAPPED IN ORGANOPOLYSILOXANE MATRIX FOR TREATING INTESTINAL DISEASES

CROSS-REFERENCE TO RELATED APPLICATIONS

The patent application is a 35 U.S.C. § 371 National Phase Application of International Patent Application No. PCT/US2019/037694, filed Jun. 18, 2019, claiming the benefit of U.S. provisional application 62/686,734, filed Jun. 19, 2018, which are incorporated herein by reference in their entireties.

TECHNICAL FIELD

Compositions comprising bioactive enzymes entrapped in organopolysiloxane matrix and methods for treating intestinal diseases, and methods for entrapping the enzymes in the organopolysiloxane matrix.

BACKGROUND

Orally delivered enzymes have a potential as therapeutics for treating gut lumen diseases, including inflammatory intestinal diseases such as inflammatory bowel disease (IBD), ulcerative colitis and Crohn's disease. Orally delivered enzymes may also help patients with pancreatic insufficiency. Bioactive enzymes may be also used for silencing the microbiome quorum signaling which is believed to play an important role in community related microbial behaviors, including biofilm formation and maintenance, virulence and microbial swarming in the gut lumen. In Gram negative bacteria, quorum signals are typically carried by acylhomoserine lactones. In Gram positive bacteria, quorum signals are typically carried by small post translationally modified secreted peptides.

Certain enzymes, including, but not limited to, acylhomoserine lactone hydrolases and organophosphate hydrolases are effective at hydrolyzing acylhomoserine lactone molecules. In vitro experiments in model systems have shown that quorum responsive microbial processes such as biofilm formation in *Pseudomonas aeruginosa* and pigment formation in *Chromobacterium violaciens* can be inhibited when cultures of these Gram negative bacteria are treated with enzymes capable of hydrolyzing acylhomoserine lactones.

In the case of Gram positive organisms within the microbiome, post translationally modified peptides from the Com C gene are secreted and act to carry quorum signals between Gram positive organisms. While highly diverse among strains of Gram positive bacteria, the Com C peptide possess a consensus sequence (EXXA/GE) in the mature secreted peptide which can be recognized by trypsin-like proteases. Proteolytic degradation of the Com C peptide results in the silencing of Gram positive microbe dependent quorum signals. Quorum signals derived from Gram positive or Gram negative organisms can also influence other microorganisms. Therefore, Gram positive organisms can respond to Gram negative quorum related responses and vice versa.

Certain enzymes, including trypsin-like proteases, acylhomoserine lactone hydrolases and organophosphate hydrolases, may find an application in controlling signaling of Gram negative and Gram positive bacteria in gut.

However, it is difficult, if not impossible, to orally deliver bioactive enzymes to the lower gut of a patient because proteins, including enzymes, are efficiently denatured and degraded in the upper gut.

In order to stabilize an enzyme, enzyme immobilization to a certain support can be used. A number of materials and techniques have been developed for enzyme immobilization, including synthetic polymer resins, natural polymers, and natural inorganic and synthetic minerals.

Overall, three enzyme immobilization processes are known: 1) physical adsorption to surfaces through electrostatic interaction, 2) chemical crosslinking to surfaces by reactive groups fixed to the surface, and 3) physical trapping of enzymes in matrices. In most cases regardless of the method employed, enzymes are loaded onto a support. Generally, the enzyme loading capacity of the support is limited by available surface area and packing density within the chosen material and is often expressed as milliequivalents of protein per support.

Immobilizing enzymes provides a number of advantages and enables a performance in enzyme-mediated processes, including resistance to denaturation, improved handling and ease of downstream processing. Despite these advantages, each immobilization support and method has limitations.

Chemisorbed enzymes are vulnerable to leaching as binding interactions are equilibrium dependent. As such, the solution environment needs to be carefully monitored to avoid enzyme wash off.

Covalent cross-linking provides a way to fix proteins permanently to the support through chemical reactions between support functional groups and specific amino acid residues found on the enzyme. The consequent covalent linkages insure that enzymes remain fixed to the surfaces. However, this approach leads to low loading densities, high costs associated with substrates and potential interference of the crosslink site with enzyme active sites. One specific unique example of crosslinking enzymes involves chemistry designed to stabilize enzyme crystals. In this case the support material is the crystalline enzyme itself which provides a theoretical upper limit for enzyme loading in a solid state.

Since at least the 1990's, enzyme entrapment in solid matrices has been used to stabilize enzyme activities and create materials that can be readily handled and recovered from solutions. The most common technique involves the entrapment of enzymes within a matrix that is assembled in situ. Polysaccharides such as alginate can be dispersed and solubilized in aqueous media that also contains co-solubilized enzymes. Calcium salts are then introduced which ligate to the alginate creating a solid matrix. While effective, alginate-based immobilization matrices are very soft and shear sensitive. In addition, these materials cannot be dehydrated and rehydrated.

As an alternative, siloxane monomers, particularly tetramethoxysilane and tetraethoxysilane, have been applied to enzyme entrapment. However, the historical limitation to siloxane-based immobilization has been that the monomers are poorly water-soluble and once they are hydrolyzed, they introduce alcohol solvents which can denature the enzymes to be entrapped. The process also calls for high shear conditions such as sonication which is needed to emulsify the siloxane monomers prior to polymerization via solution gel chemistry.

The general understanding prior to this disclosure is that siloxane-based enzyme immobilization is a difficult and costly process which cannot be scaled efficiently for commercial applications. In addition, the matrix is generally a pure silicate which has variable surface chemistry affecting morphology, pore size and chemical compatibility to enable dynamic equilibrium with the environment.

SUMMARY

In one aspect, this disclosure provides one or more quorum silencing enzymes entrapped in an organopolysiloxane matrix. The enzymes may comprise an acyl-homoserine lactone hydrolase, acyl-homoserine-lactone acylase organophosphate hydrolase, trypsin-like protease, or any combination thereof. The enzymes may possess a hydrolytic activity against acyl-homoserine lactones. The enzymes may possess a hydrolytic activity against a quorum signaling Com C peptide. The enzymes may comprise a hydrolytic activity against acyl-homoserine lactones and a hydrolytic activity against quorum signaling Com C peptides.

The organopolysiloxane matrix may comprise tetra-alkoxy siloxane moieties, trialkoxy-organosiloxane moieties, or any combinations thereof. Some embodiments provide the enzymes entrapped in the organopolysiloxane matrix is obtained by gelating a hydrolyzed siloxane pre-polymer mixture with a ratio of 50-100 mol % $Si(OR)_4$ to 50-0 mol % $Si(OR)_3R'$; wherein R is an alkoxy group and R' is selected from the group consisting of methyl, ethyl, propyl, isopropyl, butyl, octyl, hexadecyl, octadecyl, phenyl, trimethylaminopropyl, aminopropyl, aminobutyl, alkyl, mercaptopropyl, or methylphosphonyl.

Preferred embodiments include the enzymes entrapped in the organopolysiloxane matrix, wherein the organopolysiloxane matrix is obtained by gelating a hydrolyzed siloxane pre-polymer mixture comprising 70 mol % $Si(OR)_4$, 20 mol % $Si(OR)_3R'$ where R'=phenyl, and 10 mol % $Si(OR)_3R''$ where R''=trimethylaminopropyl group, and wherein R is an alkoxy group.

Further embodiments provide formulations with the entrapped enzymes, include those in the form of a lyophilized powder. The formulation may be in the form of a tablet, gel capsule, powder, suspension, slurry, injectable liquid formulation, gel, cream, chewable, suppository or syrup.

Further embodiments include methods for obtaining a quorum silencing enzyme entrapped in an organopolysiloxane matrix, the method comprising:

1) hydrolyzing a siloxane pre-polymer with water under the acidic conditions, and thereby obtaining a siloxane pre-polymer; and
2) gelating the hydrolyzed siloxane pre-polymer with one or more quorum silencing enzymes under a pH in the range from about 7 to about 10, and thereby entrapping the one or more quorum silencing enzymes in the organopolysiloxane matrix.

In some of the methods, the step of hydrolyzation is conducted in the presence of hydrochloric and/or acetic acid. In some of the methods, the siloxane pre-polymer is dissolved in methanol and/or ethanol. In some of the methods, the enzyme comprises acylhomoserine lactone hydrolase, organophosphate hydrolase, trypsin-like protease, or any combination thereof. In some of the methods, the step of hydration is conducted in the pH range from about 1 to about 6. In some of the methods, the step of hydrolyzation is conducted in the presence of an acid with a pKa below 4. In some of the methods, the step of hydrolyzation is conducted in the presence of an acid with a pKa below 4 and at a temperature in the range from 20° C. to 70° C. In some of the methods, the step of hydrolyzation is conducted in the presence of hydrochloric acid and at a temperature in the range from 50° C. to 70° C.

In some of the methods, the siloxane pre-polymer comprises:
tetra-alkoxysilane monomers with the general formula $Si(OR)_4$ (I) wherein each of the four R groups independently is methyl, ethyl,
propyl, isopropyl and/or butyl alkyl.

In some of the methods, the siloxane pre-polymer comprises:
organoalkoxysilane monomers with the general formula $Si(OR)_3R'$ (II)
wherein:
each of the three R groups independently is methyl, ethyl, propyl, isopropyl and/or butyl alkyl; and
R' is methyl, ethyl, propyl, isopropyl, butyl, octyl, hexadecyl, octadecyl,
phenyl, trimethylaminopropyl, aminopropyl, aminobutyl, alkyl,
mercaptopropyl, or methylphosphonyl.

In some of the methods, the step of gelation is carried out at a temperature in the range from about 20° C. to about 60° C.

Some of the methods may further comprise a step of gel curing and/or lyophilizing after the step of gelation.

Further aspects include a method of treating a patient, the method comprising administering to a patient a formulation comprising a quorum silencing enzyme entrapped in an organopolysiloxane matrix. The patient may be treated for at least one of the following diseases: inflammatory intestinal disease, inflammatory bowel disease (IBD), Celiac disease, gluten intolerance, ulcerative colitis, Crohn's disease, colon cancer, diabetes type I, diabetes type II, multiple sclerosis, sinus inflammation or Alzhimer's. The patient may be treated for an inflammatory intestinal disease is selected from the group consisting of inflammatory bowel disease (IBD), Celiac disease, gluten intolerance, ulcerative colitis and Crohn's disease.

The formulation in the treatment methods may be administered orally, rectally and/or by injection. The formulation in the treatment methods may be administered in the form of a tablet, gel capsule, powder, suspension, slurry, syrup, chewable, suppository and/or injectable liquid. The formulation may comprise from 0.5 mg to 800 mg of the bioactive enzyme per dosage. The bioactive enzyme may comprise an acyl-homoserine lactone hydrolase, acyl-homoserine-lactone acylase organophosphate hydrolase, trypsin-like protease, or any combination thereof. The bioactive enzyme may possess a hydrolytic activity against acyl-homoserine lactones. The bioactive enzyme may possess a hydrolytic activity against a quorum signaling Com C peptide. The bioactive enzyme may comprise a hydrolytic activity against acyl-homoserine lactones and a hydrolytic activity against quorum signaling Com C peptides.

DETAILED DESCRIPTION

The present disclosure provides compositions and methods for delivering bioactive enzymes to at least a portion of the lower gut.

In this disclosure, the "lower gut" referred interchangeably as "lower gastrointestinal tract." The lower gut is the segment of the gastrointestinal tract extending from the pyloric sphincter of the stomach of a human patient to the anus of the human patient. Typically, the lower gut consists of two segments, the small intestine and the large intestine. However, some human patients may have at least a portion of their lower gut surgically removed as part of a medical treatment.

This disclosure provides compositions and methods which overcome at least some of the limitations associated with conventional synthesis methods for entrapping bioactive enzymes in an organosilicate gel matrix. In the present methods, a pre-polymer siloxane is prepared which is water-soluble. An aqueous enzyme solution is then added directly to the pre-polymer siloxane during gelation of the pre-polymer siloxane. In the present methods, the buffer contained within the enzyme solution is used as a catalyst of organosilicate gelation. Accordingly, catalysts and solvents which are typically used for siloxane polymerization in conventional methods are avoided in the presently described methods.

The present methods for entrapping an enzyme into an organopolysiloxane matrix comprise two steps: 1) hydrolyzation of a siloxane pre-polymer; and 2) co-gelation of the hydrolyzed pre-polymer with one or more enzymes. The gelation produces one or more enzymes entrapped in the organopolysiloxane matrix.

In the present methods, a siloxane monomer or a mixture of different siloxane monomers is hydrolyzed under the acidic conditions in the pH range from about 1 to about 6. The hydrolyzation reaction is carried out in the presence of an acid. Any acid, organic or inorganic, may be used. An organic acid may be an acetic acid. The inorganic acids are preferred. One preferred inorganic acid is hydrochloric acid. However, any acid with an acid dissociation constant, pKa, below 4 may be also used.

While all hydrolyzation reactions are carried out in the presence of water and acid, some of the reactions also include an alcohol, such as methanol or ethanol, which acts as a solvent for siloxane pre-polymer. Suitable alcohols include, but are not limited to, ethanol and methanol. Other polar protic solvents may be used as well in addition or instead of ethanol and/or methanol.

The hydrolyzation reaction may be carried at a temperature in the range from room temperature (20° C.) to 70° C. At least some hydrolyzation reactions are carried out in the temperature range from about 40° C. to about 70° C. At least some hydration reactions are carried out in the temperature range from 40° C. to 70° C. Preferably, the hydration reaction is carried at 60° C.

The time of the hydrolyzation reaction may vary and may be adjusted as needed in order to complete hydrolyzation of the siloxane pre-polymer. Typically, the hydrolyzation reaction may be carried at a temperature in the range from 50° C. to 70° C. for a period of time from about 10 minutes to about 3 hours. Preferably, from about 30 minutes to 2 hours. More preferably, from 30 minutes to 2 hours. In some preferred embodiment, the hydrolyzation reaction is carried at 60° C. for one hour.

In this disclosure, if no pressure conditions are specified for a chemical reaction, a person of skill will understand that the reaction is carried out under the normal atmospheric pressure, which is the standard sea level pressure. The standard sea level pressures is 101325 Pascals.

In this disclosure if no temperature conditions are specified for a chemical reaction, a person of skill will understand that the reaction is carried out at room temperature. It will be further understood that the term "room temperature" means 20° C.

The term "acidic conditions" is applied in this disclosure broadly and includes any solution with a pH in the range from 1 to 6 as measured at room temperature. A pH of a solution may be measured with any commercially available pH meter or pH responsive dye indicator such as a pH indicating paper.

A great variety of siloxane monomers are suitable for present enzyme entrapment methods. Suitable siloxane pre-polymers are tetra-alkoxysilane pre-polymers and co-polymers include those with the general formula (I):

$$Si(OR)_4 \qquad (I)$$

wherein each of the four R groups independently is methyl, ethyl, propyl, isopropyl and/or butyl alkyl. Siloxanes with other organic and/or inorganic R groups may be also used.

Suitable siloxane pre-polymers also include pre-polymers with the general formula (II):

$$Si(OR)_3R' \qquad (II)$$

wherein:
each of the three R groups independently is methyl, ethyl, propyl, isopropyl and/or butyl alkyl; and
R' is methyl, ethyl, propyl, isopropyl, butyl, octyl, hexadecyl, octadecyl, phenyl, trimethylaminopropyl, aminopropyl, aminobutyl, alkyl, mercaptopropyl, or methylphosphonyl.

In further embodiments, an admixture of various pre-polymers of Formula (I) and Formula (II) may be used.

In this disclosure, the siloxane pre-polymer can be composed of any variation of relative concentration of tetra-alkoxy siloxanes and organotrialkoxy-organosiloxanes. The mixed pre-polymer can include in a ratio of 50-100 mol % $Si(OR)_4$ to 50-0 mol % $Si(OR)_3R'$. A preferred composition is 60 mol % $Si(OR)_4$: 40 mol % $Si(OR)_3R'$, and the most preferred composition 70 mol % $Si(OR)_4$ and 30 mol % $Si(OR)_3R'$.

Further, the pre-polymer may be composed of multiple organotrialkoxysiloxane mixtures such that the $Si(OR)_3R'$ component may be a mixture of different trialkoxy-organosiloxanes. Suitable compositions may include 70 mol % $Si(OR)_4$, 20 mol % $Si(OR)_3R'$ where R'=phenyl, and 10 mol % $Si(OR)_3R''$ where R''=trimethylaminopropyl group.

Within the scope of this disclosure, mixtures of the $Si(OR)_3R'$ component in the pre-polymer can be of multiple different organoalkoxysiloxanes, i.e. mixtures of two, three or more unique $Si(OR)_3R'$ monomers.

After the step of hydrolyzation is completed, a buffered solution comprising an enzyme or a mixture of several enzymes, hereafter refer to as the enzyme solution, is added to the hydrolyzed siloxane pre-polymer and gelation is carried on. The relative amounts of the enzyme(s) and of the hydrolyzed siloxane pre-polymer may vary, depending on an application and particular enzymes and pre-polymer to be used. Typically, the enzyme(s) and the hydrolyzed siloxane pre-polymer are reacted in molar ratios in the range from 1:1000 to 1:1, respectively.

Typically, the enzyme solution is buffered and its pH is basic, i.e. in the range from about 7 to about 10, and more preferably from 7 to 9. In some preferred embodiments, the pH of the enzyme solution is 8. Various buffers are suitable, including Tris buffers and/or Tris-phosphate buffers.

Once the enzyme solution is added to the hydrolyzed siloxane pre-polymer, the pH of the gelation mixture is increased to at least 7 or above 7, i.e. in the range from about 7 to about 10. The gelation reaction is carried at a temperature in the range from about 20° C. to about 60° C. In some embodiments, the gelation reaction is carried at a temperature in the range from about 30° C. to about 50° C. Preferably, the temperature of the gelation reaction is in the range from 30° C. to 40° C. The gelation reaction may be carried on for a period time needed for the gelation mixture to gel, i.e. for about 10 minutes to 2 hours.

One of the technical advantages of the present methods is the gelation reaction is carried in the presence of an enzyme to be entrapped. The buffer in the enzyme solution serves as a catalyst. Accordingly, the use of additional other catalysts may be avoided. However, an additional catalyst may be used in some embodiments.

The exact time needed for the gelation reaction depends on various parameters, including a temperature at which the gelation reaction is carried out and a composition of the hydrolyzed siloxane pre-polymer.

The resulting siloxane polymer is useful as a matrix to effectively physically trap and immobilize enzyme molecules. The immobilized enzyme molecules of the present disclosure are protected by the matrix from local environmental conditions including pH, and denaturants such as organic solvents and detergents. Further, the pore size of the matrix is too small and protease enzymes cannot access and degrade the enzymes entrapped in the matrix. At the same time, the entrapped enzymes remain bioactive. Yet another technical advantage of the present method is that the entrapped enzymes are too large to cross gut tissues barriers and thus do not absorb into the patient's blood and remain located in the lower gut until evacuated by bowel movement.

Mixing various alkoxysiloxane monomers with different organic groups results in the preparation of tailored matrices and provides a control of the local chemical environment of the matrix surrounding the enzyme. In addition, the tailored siloxane environment can impart specific chemical properties to improve the enzyme-silicate performance as needed in a given application.

Various enzymes may be entrapped accordingly to the present methods, including lactonases, organophosphate hydrolases, acylases and trypsin proteases. Other Gram positive and/or Gram negative quorum silencing enzymes and/or their combinations may be used as well.

Quorum silencing enzymes in this disclosure include enzymes, catalytic domains of enzymes and enzyme derivatives which have been modified by recombinant technologies, i.e., in order to improve stability, resistance to degradation, improved catalytic activity. Any enzyme which can be used to disrupt at least partially a signaling process in a bacterial population is referred to in this disclosure as a quorum silencing enzyme.

Any of the following enzymes or their catalytically active derivatives may be entrapped in the organopolysiloxane matrix of this disclosure:
  Trypsin (EC 3.4.21.4), a serine protease from the PA clan superfamily, including trypsin obtained from the bovine pancreas;
  Quorum-quenching N-acyl-homoserine lactonase (EC 3.1.1.81);
  Acyl-homoserine-lactone acylase (EC 3.5.1.97); and
  Aryldialkylphosphatase (EC 3.1.8.1).
  Suitable enzymes also include Acylhomoserine lactonase from *Bacillus* sp., Acylhomoserine acylase from *Pseudomonas* sp. Organophosphate hydrolase from *Geobacillus stearothermophilus* and trypsin from the bovine pancreas.

Once the gelation step is completed and quorum silencing enzymes are entrapped in the organopolysiloxane matrix, the preparation is cured and solidified. Curing may be conducted at a lower temperature, i.e. below room temperature. Typically, the curing may be conducted at 4° C.

The cured solid comprising the entrapped quorum silencing enzyme may be then frozen and lyophilized into a powder which comprises silencing enzymes entrapped in the organopolysiloxane matrix. The powdered matrix can be dehydrated and rehydrated under defined conditions once gelation and ripening have been completed. This provides an additional technical advantage for the methods of this disclosure as prior art methods typically do not allow for rehydration.

The powder may be pressed into tablets and coated. Other oral formulations may be prepared as well, such as for example, a slurry and/or suspension, gel capsules, powder, pills, chewables or syrup.

Any of techniques known to a person of skill for preparing an oral formulation may be used. In some embodiments, the lyophilized power may be combined with at least one or more from an excipient, dispersant, flavoring agent, pH stabilizer, and/or a bulk filler. Pressed tablets and/or coated gel capsules may be prepared, according to any of the procedures typically used by a person of skill. Other formulations may include a rectal suppository, cream, gel or a formulation which can be administered with an enema. Other administration routes may include injections and direct delivery of a formulation to the lower gut, wherein the formulation is loaded on at least one medical device inserted into a patient. Accordingly, a formulation may be an injectable liquid formulation or powder formulation combined with a liquid excipient as needed prior to administration.

The action of enzymes to degrade quorum signaling molecules known as quorum quenching, which is also referred to as quorum silencing interchangeably in this disclosure, provides a selective means to reduce concentration of these molecules in vivo. Enzymes capable of hydrolyzing quorum signaling molecules need to be protected from harsh environments and proteolytic degradation that occurs in the upper gut prior to delivery to site of action in the lower intestines. To this end engineered silicate matrices are described in this disclosure to immobilize quorum quenching enzymes and provide a platform by which these enzymes can be delivered to the microbiome while remain bioactive. The matrix entrapped enzyme used as the quorum silencer is stabilized against inactivation by denaturation or proteolytic digestion through the physical barrier, buffering and pore size characteristics of the inert silica scaffold. This quorum signal silencing strategy offers the advantage of acting at site of need without the risk of migration to the rest of the body via adsorption which may be the case for small molecule quorum inhibitors. Furthermore, the silica matrix protects the entrapped enzymes from degradation by gastric fluids.

Various diseases may be treated with formulations comprising quorum silencing enzymes. The present formulations comprising quorum silencing enzymes entrapped in the organopolysiloxane matrix may be used to treat a patient whose gut microbiome is abnormal. Such patients include those who are diagnosed with the gut microbiome dysbiosis. The term "gut microbiome dysbiosis" is used in this disclosure broadly and includes any condition under which there is an imbalance in the gut microflora. The gut microbiome dysbiosis may include an overgrowth of bacteria and/or yeast strains. Other causes of the imbalance in the gut microflora include an undergrowth of gut bacteria and/or yeast and/or a growth of bacteria and/or yeast in the gut area such as small intestine. A patient with the gut microbiome dysbiosis may be treated with a formulation comprising one or more quorum silencing enzymes entrapped in the organopolysiloxane matrix, as provided in this disclosure.

Diseases that can be treated with the formulations of the present disclosure include, but are not limited, to intestinal inflammatory diseases and/or any other diseases, symptoms of which may be ameliorated by improving the balance in the gut microbiome. Intestinal inflammatory diseases that can be treated with the formulations include inflammatory bowel disease, Celiac disease, gluten intolerance, ulcerative colitis and Crohn's disease. Other intestinal diseases include colon cancer and any other intestinal cancers. Yet other diseases that may be treated with the present formulations include diabetes type I or type II, multiple sclerosis, sinus infections, Alzheimer's and any other disease in which the gut microbiome is abnormal as the gut microbiome may be corrected with the bioactive quorum silencing enzymes entrapped in the organopolysiloxane matrix, as provided in this disclosure. The "abnormal gut microbiome" is understood broadly and includes any imbalance in the gut microbiome, such as a change in microbial species and/or a change in a number (a decrease or increase) and/or a growth in the gut areas not commonly occupied by microflora. The abnormal gut microbiome may be tested via a number of tests commonly known to a medical practitioner, for example, a microflora from a stool sample may be cultivated and analyzed for microbial species and and a number.

Methods of treatment include administering to a patient in need of treatment for abnormal gut microbiome, a formulation comprising one or more quorum silencing enzyme entrapped in the organopolysiloxane matrix, obtained as described in this disclosure. Intestinal inflammatory diseases that can be treated with the formulations include inflammatory bowel disease, Celiac disease, gluten intolerance, ulcerative colitis and Crohn's disease. Other intestinal diseases include colon cancer and any other intestinal cancers. Yet other diseases that may be treated with the present formulations include diabetes type I or type II, multiple sclerosis, sinus infections and Alzheimer's.

The formulation may be administered as an oral formulation and/or as a rectal suppository, by enema, by direct injection or delivered directly to the lower gut with by a medical device. The one or more quorum silencing enzymes entrapped in the organopolysiloxane matrix are administered in an effective amount which is any amount sufficient to at least partially decrease inflammation in the lower gut and/or at least partially silence a signaling between bacteria at least in a portion of the patient's lower gut.

In some treatment methods, the effective amount of a bioactive enzyme may be any amount in the range from about 0.5 mg to 200 mg of the bioactive enzyme per one dosage if formulated as a gel capsule. Tablets may have effective bioactive enzyme dosages from 0.5 mg to 800 mg per dosage. Chewable formulations may have dosages from 0.5 mg to 200 mg per dosage. Liquid suspensions may have dosages from 0.5 mg per mL to 50 mg per mL per dosage. The total effective amount administered per day may vary, depending on various factors, including the patient's condition, weight and response to the treatment. A dosage may be increased or decreased, as needed.

Methods of treatment include administering to a patient in need of a treatment for an inflammatory intestinal disease, an oral formulation and/or a formulation administered as a rectal suppository or by enema, the formulation comprising one or more quorum silencing enzyme entrapped in the organopolysiloxane matrix, obtained as described in this disclosure.

Example 1. Preparation of an Enzyme Entrapped in an Organopolysiloxane Matrix

A 1 gram mixture of tetraethoxysilane (TEOS):phenyltrimethoxysilane (PTMS):trimethylaminopropyltrimethoxysilane (TMAPTMS), in a mole ratio of 70:20:10 is added to 20 ml MEOH followed by 0.05 ml deionized $H_2O$ and 0.025 ml 0.1M aqueous HCL. The reaction is stirred and heated to 60° C. for 1 hour. The temperature is elevated to reflux and the MEOH is distilled off to be replaced by an equivalent amount of deionized $H_2O$ over 1 hour. The aqueous solution is then cooled to room temperature. To the cooled solution is added 1 ml of 1 mg/ml enzyme solution in 0.2M pH 8 Tris buffer. The matrix is allowed to gel at 30° C. until set and then the solid matrix allowed to cure at 4° C.

Cured solid is then frozen at −80° C. and then lyophilized to yield a white to off white powder. Representative examples of enzymes that can be immobilized in the matrix include: Acylhomoserine lactonase from *Bacillus* sp., Acylhomoserine acylase from *Pseudomonas* sp. Organophosphorus hydrolase from *Geobacillus stearothermophilus*, and/or Trypsin from bovine pancreas. Further representative examples of enzymes immobilized in the silicate matrix include a combination of both gram negative and gram positive silencing enzymes listed above.

Example 2. Preparation of Enteric Coated Enzyme Entrapped in Silicate Matrix 50 mg of a powdered silicate matrix containing the entrapped enzyme prepared in Example 1 is dispersed in 5 ml of a 0.05M Phosphate buffer pH 7. In a separate vessel, 10 mg of Eudragit S100 polymer is dispersed in 1 ml of $diH_2O$ and solubilized by titrating with 0.1M NaOH. The polymer is added to the stirred silicate dispersion dropwise and the water in the final solution is removed under reduced pressure. The resulting polymer coated silicate powder is ready for use as an enteric stable material.

REFERENCES

Lloyd-Price, J., Abu-Ali, G., & Huttenhower, C. The healthy human microbiome. *Genome Medicine,* 2016, 8, 51. http://doi.org/10.1186/s13073-016-0307-y T. B. Rasmussen, Bjarnsholt, T., Skindersoe, M. E., Hentzer, M., Kristoffersen, P., Ko¨te, M., Nielsen, J., Eberl, J., Givskov, M., Screening for Quorum-Sensing Inhibitors (QSI) by Use of a Novel Genetic System, the QSI Selector. *J. Bacteriol.* March 2005, 187, 1799-1814.

Miller, M. B., Bassler, B. L., Quorum sensing in bacteria. *Ann. Rev. Microbiol.* 2001, 55, 165-199.

Pei, W. T., Stone, E. M., Costello, A. L., Tierney, D. L., Fast, W., The quorum-quenching lactonase from *Bacillus Thuringiensis* is a metalloprotein., *Biochemistry,* 2005, 44, 7559-7569.

Smith, R. S., Iglewski, B. H., *P. aeruginosa* quorum sensing systems and virulence. *Curr. Opin. Microbiol.* 2003, 6, 56-60.

Momb, J., Thomas, P. W., Breece, R. M., Tierney, D. L., Fast, W., The quorum quenching metallolactonase from *Bacillus thuringiensis* exhibits a leaving group thio effect. *Biochemistry,* 2006, 45, 13385-13393.

Jessica A. Thompson, Rita A. Oliveira, and Karina B. Xavier, Chemical conversations in the gut microbiota, *Gut Microbes* 2016, 7, 2, 163-170 http://dx.doi.org/10.1080/19490976.2016.1145374

Dong Y-H and Zhang L-H, Quorum Sensing and Quorum-Quenching Enzymes. *J Microbiol* 2005. 43(S) 101-109

Hawwa, R, Aikens, J., Turner, R. J., Santarsiero, B. D., Mesecar, A. D. Structural basis for thermostability revealed through the identification and characterization of a highly thermostable phosphotriesterase-like lactonase from *Geobacillus Stearothermophilus*. *Arch. Biochem. Biophys.* 2009, 488, 109-120.

Fetzner, S. Quorum quenching enzymes (2015) *J. Biotechnol.* 201 2-14.

Ulrich, R. L., Quorum quenching: enzymatic disruption of the quorum quenching N-acyl homoserine lactone hydrolase from *Bacillus thuringiensis*. *Appl. Environ. Microbiol.* 2004, 70, 6173-6180.

Fieker, A., Philpott, J., & Armand, M. Enzyme replacement therapy for pancreatic insufficiency: present and future. *Clinical and Experimental Gastroenterology*, 2011, 4, 55-73.

Bye, W., Ishaq, N, Bolin, T. D., Duncombe, V. M., and Riordan, S. M. Overgrowth of the indigenous gut microbiome and irritable bowel syndrome. *World J. Gastroenterol.* 2014, 20, 2449-2455.

Donlan R M and Costerton J W, Biofilms: survival mechanisms of clinically relevant microorganisms. *Clin Microbiol Rev* 2002. 15:167-193.

Venturi V, Regulation of Quorum Sensing in *Pseudomonas*. FEMS Microbiol Rev 2006. 30:274-291.

Dong Y H, Wang L H, Xu J L, Zhang H B, Zhang X F and Zhang L H, *Quenching quorum-sensing-dependent bacterial infection by an N-acyl homoserine lactonase*. Nature 2001. 411:813-817.

Lin Y H, Xu J L, Hu J, Wang L H, Ong S L, Leadbetter J R, and Zhang L H, Acyl-homoserine lactone acylase from *Ralstonia* strain XJ12B represents a novel and potent class of quorum-quenching enzymes. Mol. Microbiol 2003. 47:849-860.

Park S Y, Lee S J, Oh T K, Oh J W, Koo B T, Yum D Y and Lee J K, *AhID, an N-acylhomoserine lactonase in Arthrobacter sp., and predicted homologues in other bacteria*. Microbiol 2003. 149:1541-1550.

Roche D M, et al., *Communications blackout? Do N-acyl-homoserinelactone-degrading enzymes have any role in quorum sensing?* Microbiol 2004. 150:2023-2028.

Wang L H, Weng L X, Dong Y H and Zhang L H, Specificity and enzyme kinetics of the quorum-quenching N-Acyl homoserine lactone lactonase (AHL-lactonase). J Biol Chem 2004. 279:13645-13651.

Lichstein H C and van de Sand V F, Violacein, an antibiotic pigment produced by *Chromobacterium violaceum*. *J. Infect. Dis* 1945. 76:47-51.

Ellerby L. M, Nishida C. R, Nishida F, Yamanaka S. A, Dunn B, Valentine J. S, Zink J. I. Encapsulation of proteins in transparent porous silicate glasses prepared by the sol-gel method. *Science*, 1992, 28, 255, (5048), 1113-1115.

Massari, A. M., Finkelstein, I. J., & Fayer, M. D. (2006). Dynamics of Proteins Encapsulated in Silica Sol-gel Glasses Studied with IR Vibrational Echo Spectroscopy. *Journal of the American Chemical Society*, 128(12), 3990-3997.

Calabretta, P. J., Chancellor, M. C., Torres, C., Abel, G. R., Niehaus, C., Birtwhistle, N. J., Eggers, D. K. Silica as a Matrix for Encapsulating Proteins: Surface Effects on Protein Structure Assessed by Circular Dichroism Spectroscopy. *Journal of Functional Biomaterials*, 2012, 3, 514-527. http://doi.org/10.3390/jfb3030514

Liu D, B. W. Lepore, G. A. Petsko, P. W. Thomas, E. M. Stone, W. Fast, D. Ringe. Three-dimensional structure of the quorum-quenching N-acyl homoserine lactone hydrolase from *Bacillus thuringiensis*. Proc Natl Acad Sci USA 2005, 102(33) 11882-11887.

What is claimed is:

1. One or more quorum silencing enzymes entrapped in an organopolysiloxane matrix assembled in situ, wherein:
   the quorum silencing enzymes are an acyl-homoserine lactone hydrolase; and
   the organopolysiloxane matrix comprises tetra-alkoxy siloxane moieties, trialkoxy-organosiloxane moieties, or a combination thereof, wherein the organopolysiloxane matrix is obtained by gelating a hydrolyzed siloxane pre-polymer mixture having a ratio of 60-70 mol % of one or more tetraalkoxysilane monomers having the general formula $Si(OR)_4$ to 40-30 mol % of one or more trialkoxy-organosiloxane monomers having the general formula $Si(OR)_3R'$, wherein each R group is independently selected from the group consisting of methyl, ethyl, propyl, isopropyl, and butyl alkyl, and each R' group is independently selected from the group consisting of methyl, ethyl, propyl, isopropyl, butyl, octyl, hexadecyl, octadecyl, phenyl, trimethylaminopropyl, aminopropyl, aminobutyl, alkyl, mercaptopropyl, and methylphosphonyl; and
   the quorum silencing enzymes and the hydrolyzed siloxane pre-polymer are at a molar ratio in a range from 1:1000 to 1:1, respectively.

2. The one or more quorum silencing enzymes entrapped in an organopolysiloxane matrix assembled in situ of claim 1, wherein the hydrolyzed siloxane pre-polymer mixture comprises two of the trialkoxy-organsiloxane monomers, wherein R' is phenyl for the first trialkoxy-organosiloxane monomer and R' is trimethylaminopropyl for the second trialkoxy-organosiloxane monomer.

3. The one or more quorum silencing enzymes entrapped in an organopolysiloxane matrix assembled in situ of claim 1 in the form of a lyophilized powder.

4. A formulation comprising the one or more quorum silencing enzymes entrapped in an organopolysiloxane matrix assembled in situ of claim 1.

5. The formulation of claim 4, wherein the formulation is in the form of a tablet, gel capsule, powder, suspension, slurry, injectable liquid formulation, gel, cream, chewable, suppository or syrup.

* * * * *